US00PP25107P3

(12) United States Plant Patent
Knight et al.

(10) Patent No.: US PP25,107 P3
(45) Date of Patent: Nov. 25, 2014

(54) CRAPEMYRTLE PLANT NAMED 'CREC-0001'

(50) Latin Name: *Lagerstroemia: L. indica×L. fauriei×L. limii. 'Tonto'×L. indica 'Catawba'*
Varietal Denomination: CREC-0001

(71) Applicants: Patricia R. Knight, Biloxi, MS (US); Wayne J. McLaurin, Poplarville, MS (US)

(72) Inventors: Patricia R. Knight, Biloxi, MS (US); Wayne J. McLaurin, Poplarville, MS (US)

(73) Assignee: Mississippi State University, Mississippi State, MS (US)

( * ) Notice: Subject to any disclaimer, the term of this patent is extended or adjusted under 35 U.S.C. 154(b) by 0 days.

(21) Appl. No.: 13/573,603

(22) Filed: Sep. 27, 2012

(65) Prior Publication Data

US 2013/0104269 P1 Apr. 25, 2013

Related U.S. Application Data

(60) Provisional application No. 61/626,484, filed on Sep. 27, 2011.

(51) Int. Cl.
*A01H 5/00* (2006.01)
*A01H 5/02* (2006.01)

(52) U.S. Cl.
CPC ..... *A01H 5/02* (2013.01)
USPC ..... Plt./252

(58) Field of Classification Search
USPC ..... Plt./252
See application file for complete search history.

*Primary Examiner* — Kent L Bell
(74) *Attorney, Agent, or Firm* — Lawrence Arthur Schemmel

(57) ABSTRACT

A new and distinct cultivar of *Lagerstroemia* crapemyrtle plant named 'CREC-0001', characterized by its medium to dark purple color flowers and medium to large growth habit.

4 Drawing Sheets

STATEMENT OF GOVERNMENT SUPPORT

This invention was made with government support under 58-6404-0-014 awarded by the U.S. Department of Agriculture Agricultural Research Service. The government may have certain rights in the invention.

Botanical classification: *Lagerstroemia: L. indica×L. fauriei×L. limii*. 'Tonto'×*L. indica* 'Catawba'.

Cultivar denomination: Crapemyrtle 'CREC-0001'.

BACKGROUND OF THE INVENTION

The present invention relates to a new and distinct cultivar of the ornamental flowering shrub and landscape plant of the genus *Lagerstroemia*, commonly known as crapemyrtle, of the family Lythraceae, and is referred to hereinafter by its cultivar denomination 'CREC-0001'. This novel plant is an asexually propagated hybrid of crapemyrtle that was selected in 2008 from approximately 2800 crosses. The female seed parent is *Lagerstroemia indica×L. fauriei* 'Tonto' (unpatented). The male pollen parent is *Lagerstroemia indica* 'Catawba' (unpatented). 'CREC-0001' was selected for its unique medium to dark purple flower color and medium to large growth habit. The designation 'CREC-0001' was evaluated under the experimental number '2008-0001' and experimental name 'CREC-0001'. This high quality novel and distinct cultivar of crapemyrtle plant was vegetatively propagated in Poplarville, Miss. using vegetative medial cuttings, as opposed to tip cuttings, taken from semi-hard, current season's growth. Stem diameters were approximately ⅛ to ¼ inch. Each of several generations of cuttings has produced stable plants identical to the original seedling plant.

SUMMARY OF THE INVENTION

The new cultivar is a *Lagerstroemia* hybrid resulting from the cross of *Lagerstroemia: L. indica×L. fauriei×L. limii* 'Tonto' (female parent)×*L. indica* 'Catawba' (male parent). 'CREC-0001' is a distinctive, new cultivar of crapemyrtle plant characterized by its medium to dark purple flower color and medium to large crapemyrtle growth habit. The traits of the new plant are continually maintained when propagated asexually. This new cultivar may vary slightly with changes in location, temperature, light, and other environmental conditions, but the genotype will not be affected. 'CREC-0001' also exhibits the quality and characteristic of adaptability to all areas of hardiness zones 7-10, based on observed temperatures at the growing locations compared to the USDA Hardiness Zone map. 'CREC-0001' is much taller than its female parent 'Tonto' and its male parent 'Catawba'. 'Tonto' is a large shrub ranging from 5 to 10 feet in height. 'Tonto' has red to fuchsia flowers and maroon fall color. 'Catawba', the male pollen parent, is a small-sized crapemyrtle averaging 8 to 10 feet in height. 'Catawba' has violet purple flowers and red orange fall color. Flower color for 'CREC-0001' is more purple than either parent. This new plant has unique flower color contained in a medium to large growing crapemyrtle. The combination of 'CREC-0001's medium to dark purple flower color and medium to large growth habit distinguishes it from all other crapemyrtle cultivars known to the inventors.

BRIEF DESCRIPTION OF THE DRAWINGS

The color photographs of FIG. 1 through FIG. 4 illustrate the overall appearance and unique characteristic of medium to dark purple flower color of the new crapemyrtle cultivar 'CREC-0001'. The photographs were taken using conventional techniques and, although colors may appear different from actual colors due to light reflectance, the new plant and its colors are shown as true and accurately as reasonably possible by conventional photographic techniques. Colors in the photographs may differ from the actual colors and values in the description of the new crapemyrtle plant due to light conditions and other factors. The photographs and the detailed description of the invention are intended to illustrate further the invention and its advantages.

DETAILED BOTANICAL DESCRIPTION OF THE VARIETY

Latin name: *Lagerstroemia*×'CREC-0001'

*Lagerstroemia: L. indica*×*L. faurieiiL. limii*. 'Tonto'×*Lagerstroemia indica* 'Catawba'

Cultivar denomination: 'CREC-0001'

The present invention is a novel *Lagerstroemia*×'CREC-0001' cultivar known as 'CREC-0001' that is different from other crapemyrtle cultivars.

TON×CAT 0001 Row 01—Replication 1—Plant# 1 in Rep. McNeill planting.

The following is a detailed botanical description of the characteristics of the new *Lagerstroemia* crapemyrtle cultivar known as 'CREC-0001', based on observations of the plant grown at Poplarville, Miss., and under similar conditions to those for growing these plants commercially. 'CREC-0001' has been observed under many but not all possible environmental conditions. Color notations of plant tissues are based upon The Royal Horticultural Society (R.H.S.) Colour Chart, 2001 Edition. Color notations may have been slightly affected by light quality and fertility and general plant growth. Certain characteristics will vary depending on the age of the plants so that dimensions, sizes, and colors are approximations or averages since the cultivar has not been observed under every possible environmental condition. Therefore the phenotype of the cultivar may differ from the descriptions depending upon environmental variations including, but not limited to, the season, temperatures, day lengths, light direction and quality, and fertilization, as well as other factors.

The present invention is a *Lagerstroemia* hybrid resulting from the cross of *Lagerstroemia: L. indica*×*L. faurieiiL. limii*. 'Tonto' (female parent)×*Lagerstroemia indica* 'Catawba' (male parent). The stem color of this new plant is Royal Horticultural Society (R.H.S.) Colour Chart Group 176-A. The average total height is 8.0 feet, soil to first branch average is 15.0 inches, and the first branch to tip average is 66.8 inches. The average caliper at 6 inches is 0.79 inches, average stem length at 3 inches is 57.00 inches, and the average yearly growth is 49.40 inches. The average stem caliper at 3 inches is 0.53 inches and the average internode length is 1.55 inches, although internode lengths are subjective since they depend on factors such as sun exposure, nutrition, pruning, and the like. Stem texture is smooth to exfoliating. The leaf top color is R.H.S. Colour Chart Group 138-A. The flower petal color is medium to dark purple (R.H.S. Colour Chart Group N78-A). This new plant is a crapemyrtle with unique purple flower color that may be used as a specimen in landscapes where crapemyrtles are traditionally used. This crapemyrtle plant will be in the fifteen plus (15+) foot range for growth. Currently, not many crapemyrtles exist that are "medium to dark purples" and that are in this growth range known to the inventors.

Figure 1:
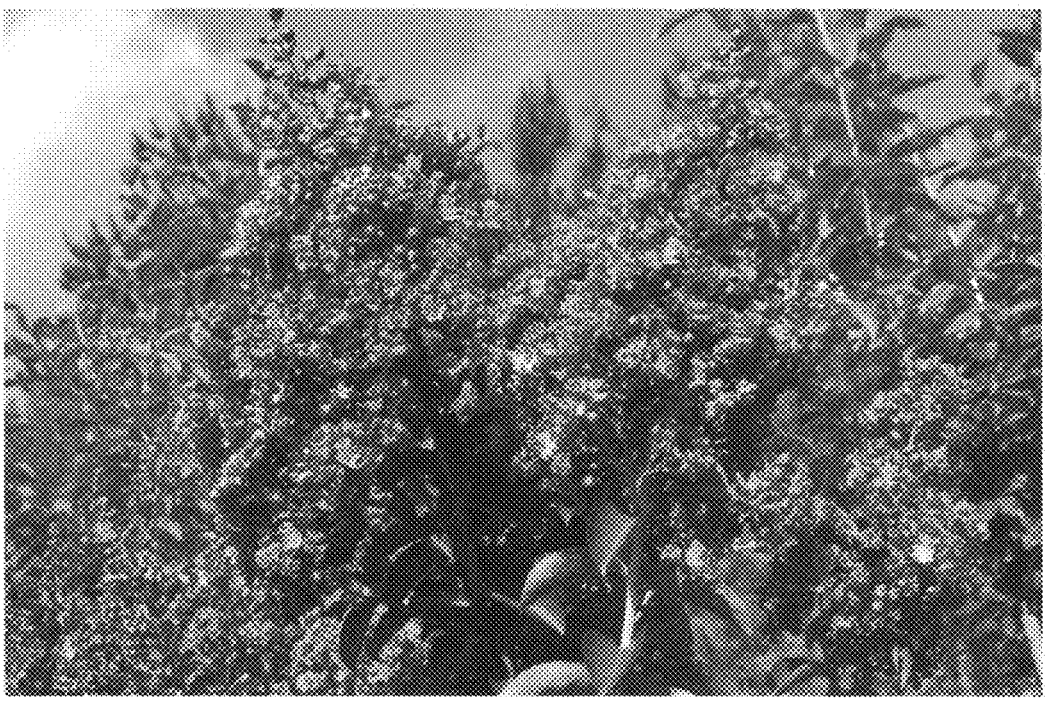
FIG. 1 is a color photograph of the new crapemyrtle 'CREC-0001' taken at Poplarville, Miss. that shows the flower and leaf color of the new cultivar.
Figure 2:
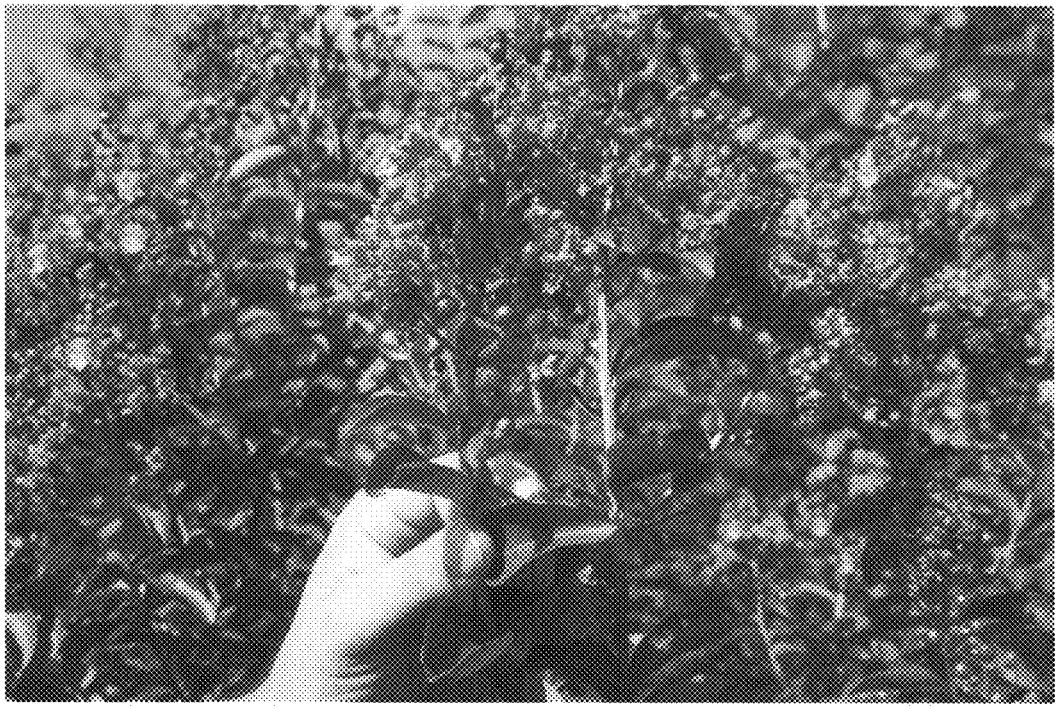
FIG. 2 is a color photograph of the new crapemyrtle 'CREC-0001' taken at Poplarville, Miss. that shows the flower and leaf color of the new cultivar.
Figure 3:
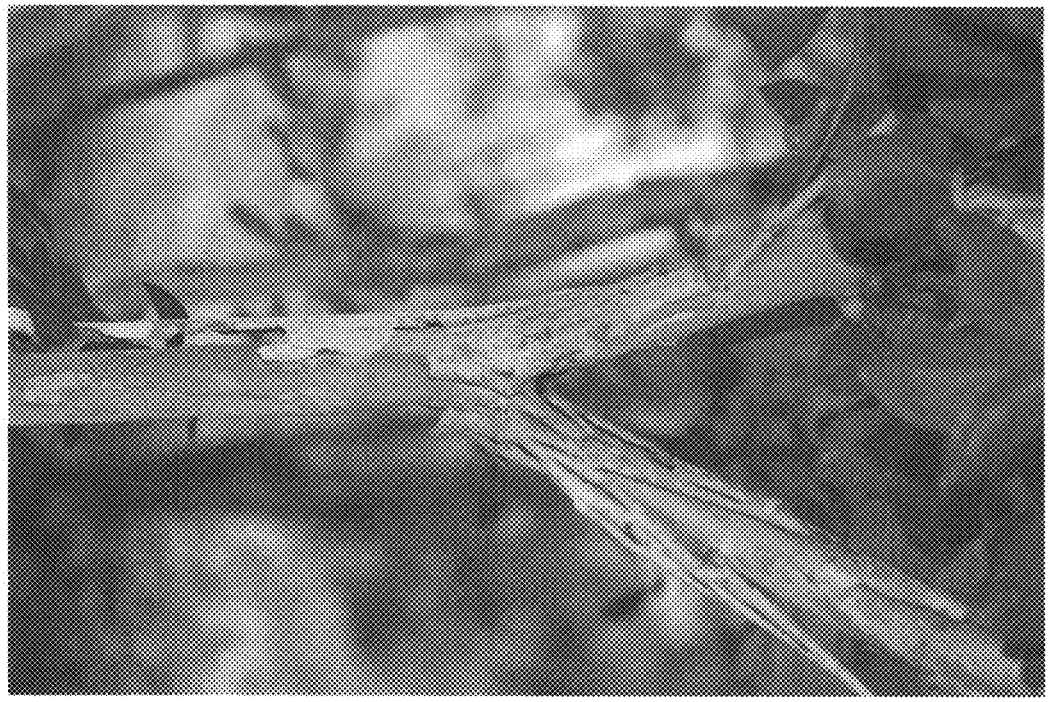
FIG. 3 is a color photograph of the new crapemyrtle 'CREC-0001' taken at Poplarville, Miss. that illustrates leaf and stem color of the new plant.
Figure 4:
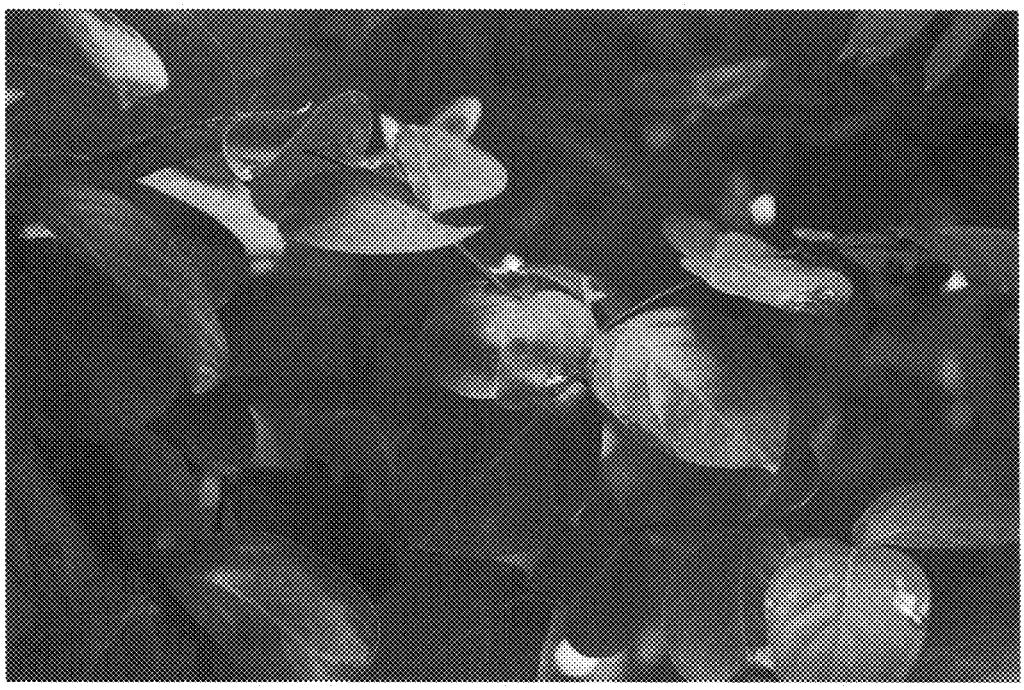
FIG. 4 is a color photograph of the new crapemyrtle 'CREC-0001' taken at Poplarville, Miss. that illustrates leaf and stem color of the new plant.

FIGS. 1 and 2 show the flower color and the leaf color of the new cultivar. FIG. 3 shows the leaf color and stem color of the new cultivar. FIG. 4 shows the leaf color and stem color of the new plant.

The final height and width of the plant have not been observed. Three-year plants in the research facility are greater than fifteen (15) feet tall and approximately 6 to 8 feet wide, forming a multiple or single trunk large crapemyrtle. The new plant has outer mature bark color in the greyed-green group in R.H.S. Colour Chart Group 196-A and inner mature bark color in the grey-brown group in R.H.S. Colour Chart Group 199-A. New stem growth is in the green group in R.H.S. Colour Chart Group 139-C. It can possibly be grown as a medium to large shrub in climates where shoot growth is killed to the ground each winter. Its foliage comprises glossy green leaves that are opposite and that are approximately from 2.50 to 3.00 inches in length and from 1.00 to 1.50 inches in width. The leaf top color is R.H.S. Colour Chart Group 138-A. The leaf underside color is R.H.S. Colour Chart Group 146-A. The leaf type is simple and is persistent and deciduous. The leaf margin is entire and the leaf venation is pinnate. The leaf apex is acute to slightly elliptical, the leaf base is rounded, and the overall shape is ovate to elliptical. New leaf color is in the green group in R.H.S. Colour Chart Group 138-A and the new leaf mid-vein color is in the green group in R.H.S. Colour Chart Group 138-B. The stem is rather slender with a slightly angular shape with prominent wings when young and a round shape when growth is more mature. The new plant is a deciduous, summer-flowering plant, so that fall color has been inconsequential. The plant has shown insect and disease tolerance comparable to the parents under field conditions.

The flowers are perfect, 6-petaled and each flower is approximately 1.30 inches in diameter. The flowers are medium to dark purple and are most typically visible from early June to late August depending on environmental conditions. Flower color represents the closest impression of the entire florescence. Individual florets are very small, so the overall impression is the observed characteristic. The flower petal color is R.H.S. Colour Chart Group N78-A. The flowers have medium tapered panicles. The flower panicle is approximately 9 to 11 inches long. The unopened flower capsule color is R.H.S. Colour Chart Group 59-A. When the flowers fade, they generally fade to lighter shades of purple, lavender, or light blue, and not to pink or red tones.

The fruit is comprised of seed pods that are dark green in color turning to brown, a mature seed pod color that is R.H.S. Colour Chart Group 144-A. The fruit is a broad-ellipsoidal 6-valved dehiscent capsule, brown in color in R.H.S. Colour Chart Group 144-A, approximately ½ of an inch wide. Seeds are approximately ⅜ to ½ of an inch long and winged. The pistil color is R.H.S. Colour Chart Group 14-A. A woody capsule generally persists on the panicle until late winter.

Cold testing in the laboratory for cold hardiness has not yet been completed for the new cultivar. Plants had just begun to exhibit the exfoliating bark characteristics common to crapemyrtles at the time of observation.

Rooting of the new medium to large-sized crapemyrtle is easily accomplished, making the plant excellent for production purposes, and such rooted plants are identical to the original. The novelty of the plant includes its medium to dark purple flower color (R.H.S. Colour Chart Group N78-A) and its medium to large size. 'CREC-0001' may be used as a specimen in landscapes where crapemyrtles are traditionally used. The new crapemyrtle plant will be in the fifteen plus (15+) foot range for growth. Currently, not many crapemyrtles exist that are this "medium to dark purple" color and that are in the medium to large crapemyrtle group growth range.

As will be apparent to those skilled in horticultural science, the new and distinct crapemyrtle plant cultivar described herein may vary in minor detail due to climatic, soil, and cultural conditions under which the variety may be grown, as well as the stage of growth.

What is claimed is:

1. A new and distinct cultivar of crapemyrtle *Lagerstroemia* hybrid plant named 'CREC-0001', substantially as herein illustrated and described.

* * * * *